(12) United States Patent
Fischer (10) Patent No.: US 6,343,929 B1
(45) Date of Patent: Feb. 5, 2002

(54) ENDODONTIC IRRIGATOR TIPS HAVING FIBER COVERED CANNULAS AND RELATED METHODS

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/766,708

(22) Filed: Jan. 22, 2001

(51) Int. Cl.⁷ .................................................. A61C 17/02
(52) U.S. Cl. .......................................... 433/81; 433/224
(58) Field of Search ........................... 433/80, 81, 102, 433/119, 224

(56) References Cited

U.S. PATENT DOCUMENTS

| | | | | |
|---|---|---|---|---|
| 5,236,358 A | * | 8/1993 | Sieffert | 433/119 |
| 5,337,463 A | | 8/1994 | Saxer et al. | 15/104.94 |
| 5,378,149 A | * | 1/1995 | Stropko | 433/80 |
| 5,693,360 A | | 12/1997 | Stern et al. | 427/2.29 |
| 5,800,367 A | | 9/1998 | Saxer et al. | 601/164 |
| 5,816,804 A | | 10/1998 | Fischer | 433/90 |
| 5,899,693 A | * | 5/1999 | Himeno et al. | 433/119 |
| 5,944,519 A | | 8/1999 | Griffiths | 433/80 |
| 6,049,934 A | | 4/2000 | Discko | 15/106 |
| 6,059,570 A | | 5/2000 | Dragan et al. | 433/80 |
| 6,082,999 A | * | 7/2000 | Tcherny et al. | 433/80 |
| 6,083,002 A | | 7/2000 | Martin et al. | 433/90 |
| 6,096,382 A | | 8/2000 | Gueret | 427/463 |
| 6,179,617 B1 | * | 1/2001 | Ruddle | 433/224 |

OTHER PUBLICATIONS

Maag, Ulrich, "Principles of Flocking," pp. 1–6, Reprinted from *Adhesives Age*, Sep. 1975, vol. 18, No. 9.
Borowski, Bob, "Get a Feel for Flocking," pp. 1–4, Reprinted from *Screen Printing*, Mar. 1998.

\* cited by examiner

*Primary Examiner*—Ralph A. Lewis
(74) *Attorney, Agent, or Firm*—Workman, Nydegger & Seeley (57) ABSTRACT

An endodontic irrigator tip with a fiber covered cannula enables a root canal be cleaned with a scrubbing action as the cannula is moved up and down within the root canal. The cannula extends from a hub that is adapted for coupling with a syringe or other delivery device. The cannula has an outlet orifice for delivering an irrigant out of the endodontic irrigator tip and into the root canal. The outlet orifice may be defined by a rounded rim that optimally enables the distal insertion end of the cannula to be advanced within the root canal.

39 Claims, 7 Drawing Sheets

FIG. 6C

ENDODONTIC IRRIGATOR TIPS HAVING FIBER COVERED CANNULAS AND RELATED METHODS

BACKGROUND OF THE INVENTION

1. The Field of the Invention

This invention is in the field of instruments for use in medicine and dentistry. More specifically, this invention is in the field of endodontic irrigator tips for irrigating root canals as part of a root canal procedure.

2. The Relevant Technology

To preserve a tooth that has a diseased pulp cavity, it is necessary to prevent bacterial proliferation within the pulp canal of the tooth by removing the diseased or necrotic pulp material from the pulp canal. After the pulp material has been removed or extirpated from a tooth, the pulp cavity is typically filled or obturated with a material such as gutta percha to occlude the pulp cavity and a sealer to seal the pulp cavity. This procedure is referred to as root canal therapy. Root canal cleaning is generally achieved by hand or mechanical instrumentation with files that are configured to bore and cut.

It is also common during the root canal procedure to irrigate a pulp cavity and the various root canals involved using an endodontic irrigator tip. Irrigation assists in removing debris and necrotic material cut by the endodontic files and bores. Disinfecting solutions can also be employed in irrigation, thereby disinfecting the pulp cavity and root canals during the operative procedure.

Although, the irrigant preferably is capable of dissolving or disrupting soft tissue remnants to permit their removal, the irrigant may be any suitable liquid such as water or various alcohols. More particularly, although some degree of débridement is preferred, any fluid may be used to flush debris from the root canal. General examples of appropriate irrigants include hydrogen peroxide, primarily for use in the canals of living teeth, or sodium hypochlorite, primarily for the canals in necrotic teeth. A preferred irrigant is the aqueous sodium hypochlorite solution sold as ChlorCid® by Ultradent Products, Inc which contains about 2.5–3% NaOCL. The irrigant may also be a chelator or calcium remover such as EDTA solutions or citric acid solutions. A preferred chelator is sold as File-Eze® by Ultradent Products Inc. which is a 19% EDTA water soluble viscous solution. File-Eze® is a preferred chelator as it is also a lubricant.

In addition to the chemical features of such irrigants, the manner in which the irrigants are delivered provides a limited physical approach to effectuating the removal of soft tissue remnants after the soft tissue has been dislodged through the use of files. More particularly, the irrigant can be sprayed in a manner which assists in further dislodging soft tissue; however, care must be used to avoid spraying the irrigant with too great of force directly into a particular location. Accordingly, the irrigant is generally used merely to flush the root canal so that soft tissue removed by the abrasive action of the files can be easily removed. There is therefore a need within the art for an endodontic irrigator tip having a cannula that can be conveniently used to mechanically remove soft tissue from the root canal while delivering an irrigant. There is a further need within the art for different irrigator tips which can be used to clean root canal surfaces that are efficient to manufacture.

Another limitation of conventional endodontic irrigator tips is the potential for the formation of ledges within the root canal. Ledges can occur when a practitioner attempts to insert the distal insertion end of an irrigator tip as far as the apex of the root canal and the distal insertion end is halted prematurely against the sidewall of the root canal. The downward pressure exerted on the distal insertion end causes the end to dig into the side of the root canal and form a ledge. Such ledges are difficult to bypass; and if the ledge occurs very close to the apex, the ledge may give the practitioner the mistaken impression that the apex has been reached. Accordingly, there is also a need for irrigator tips that can be used to physically clean root canal surfaces with minimal risk of ledging.

SUMMARY AND OBJECTS OF THE INVENTION

It is therefore an object of the invention to provide an improved endodontic irrigator tip.

It is another object of the invention to provide an endodontic irrigator tip having a cannula that can be conveniently used to mechanically remove soft tissue from the root canal while delivering an irrigant.

Another object of the invention is to provide improved distal insertion ends of irrigator tips that minimize the risk of ledging.

An additional object of the invention to provide irrigation tips that are efficient to manufacture.

The endodontic irrigator tip of the present invention comprises a cannula extending from a hub. The cannula has fibers extending circumferentially from its surface, preferably with a perpendicular orientation. The fibers are preferably on the lower portion of the cannula since this is the portion of the cannula that engages the root canal. The fibers may extend from the cannula in any configuration. However, the fibers preferably cover all of the lower half of the cannula or extend from about the midpoint of the cannula downward toward the distal insertion end of the cannula such that there are no fibers slightly above the outlet orifice of the cannula.

The hub has a body with a proximal end adapted for coupling to a syringe. The hub also has a neck having a proximal end coupled to the distal end of the body. The neck has a distal end which may be configured with a flat face to optimally prevent the placement of the irrigator tip past a desired location. A hollow chamber is located in the hub which is defined by an interior surface. The hollow chamber extends through the body and the neck and has an inlet such that fluid can be received from a syringe.

The cannula has a distal insertion end and a proximal end sheathed within the distal end of the neck. Thus, a portion of the cannula extends from the distal end of the neck with sufficient length to extend into a root canal of a tooth. An interior surface of the cannula defines a conduit in fluid communication with the hollow chamber. The cannula has an orifice located at the distal insertion end thereof. The outlet orifice is defined by a rim that is preferably rounded instead of squared.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1A:
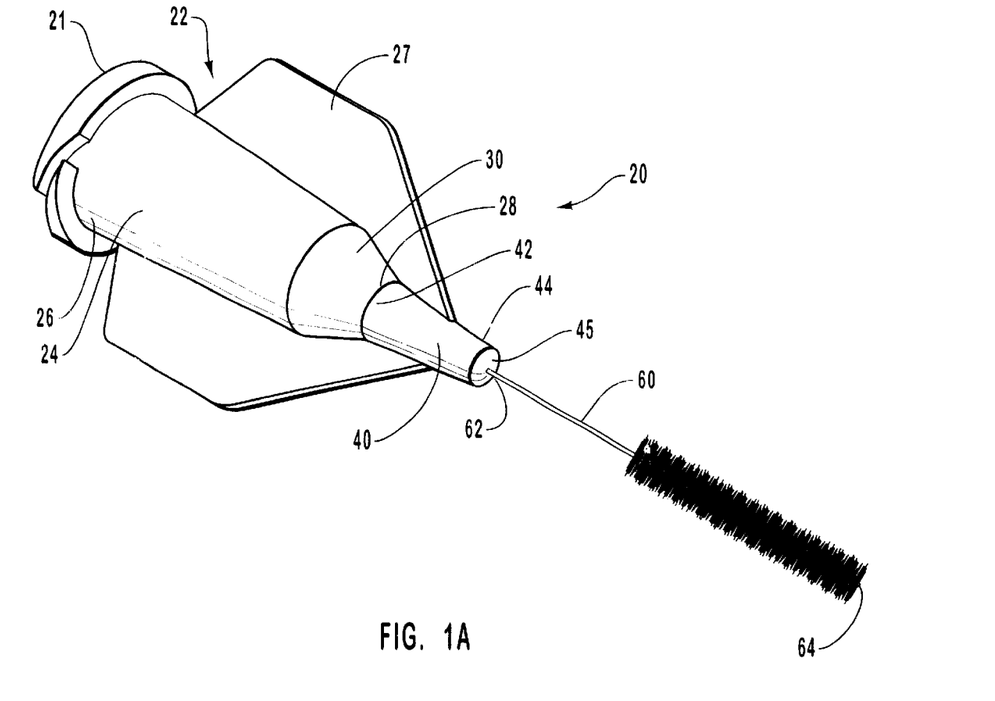
FIG. 1A is a perspective view of a fiber covered endodontic irrigator tip.
Figure 1B:
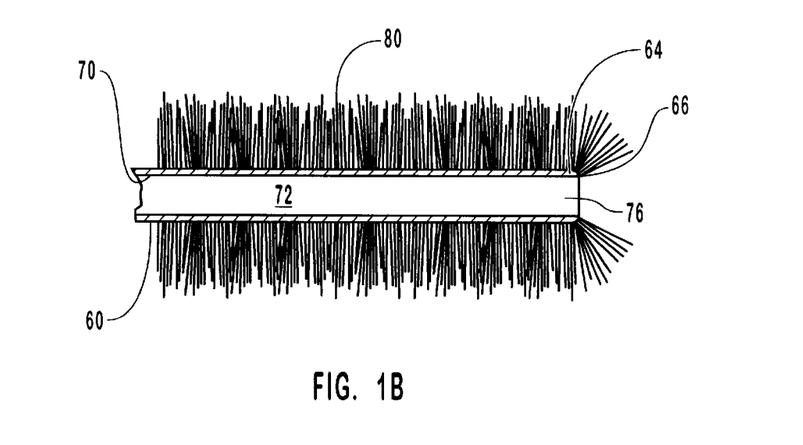
FIG. 1B is an enlarged cross sectional view of the distal insertion end shown in FIG. 1A.

An endodontic irrigator tip 20 of the present invention designed for convenient delivery of a variety of different liquids to a root canal, such as debreeding agents, lubricants, anti-bacterial agents, chelating agents, water, hypochlorites, $H_2O_2$, and EDTA is shown in FIGS. 1A–1B. The primary components of tip 20 are a hub 22, a hollow chamber 52 located within hub 22 and a cannula 60 that extends from hub 22 with fibers 80.

Fibers 80 may be positioned on cannula 60 by any suitable methodology, however, fibers 80 are preferably flocked onto cannula as described below in greater detail. Fibers 80 may be positioned on cannula 60 in various configurations. However, the majority of the lower half of the cannula is preferably covered by fibers 80. Some embodiments may not have fibers in the vicinity of the terminus of the cannula referred to herein as the distal insertion end 64.

Figure 2A:
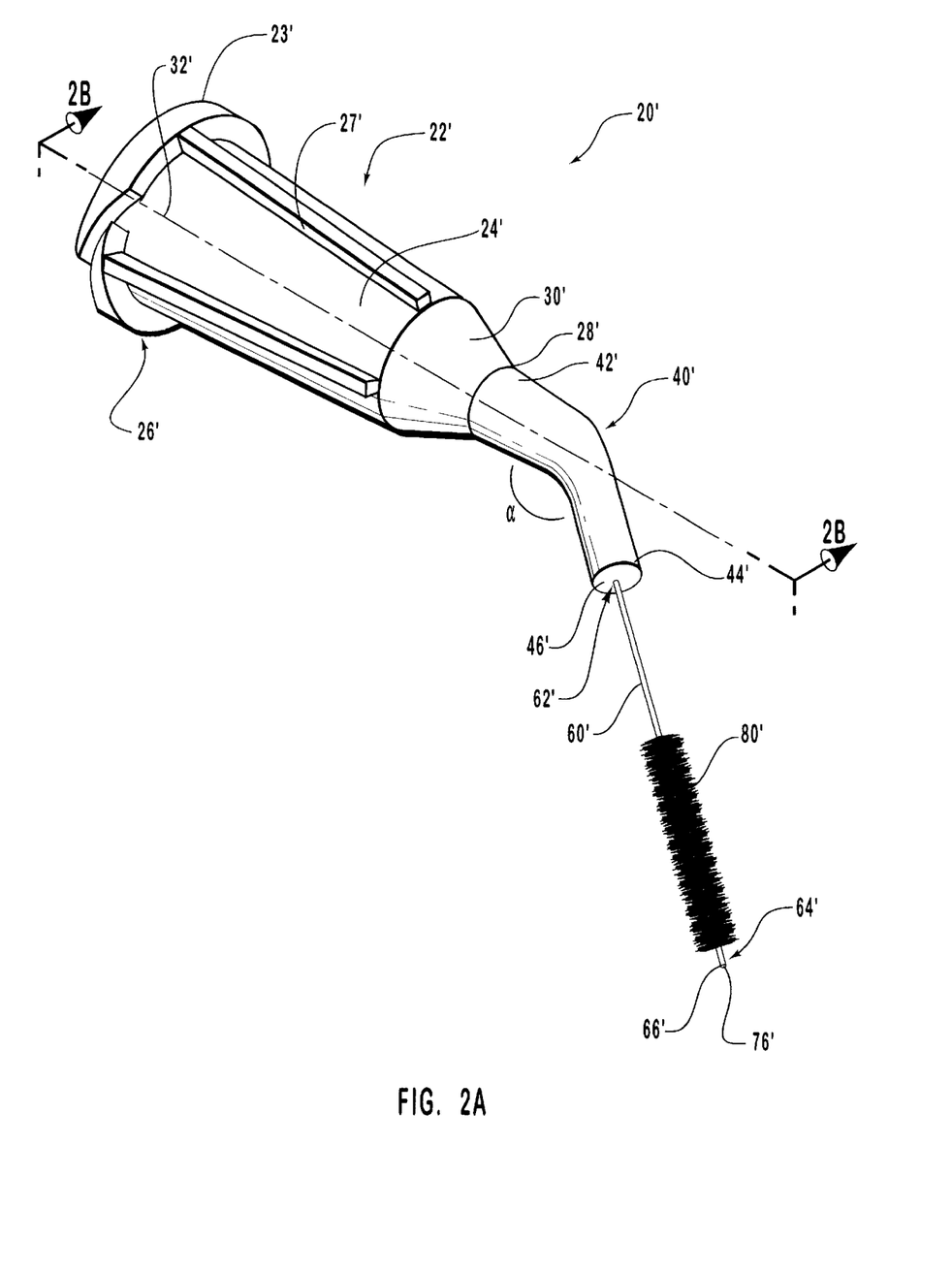
FIG. 2A is a perspective view of another fiber covered endodontic irrigator tip.
Figures 2B, 2C:
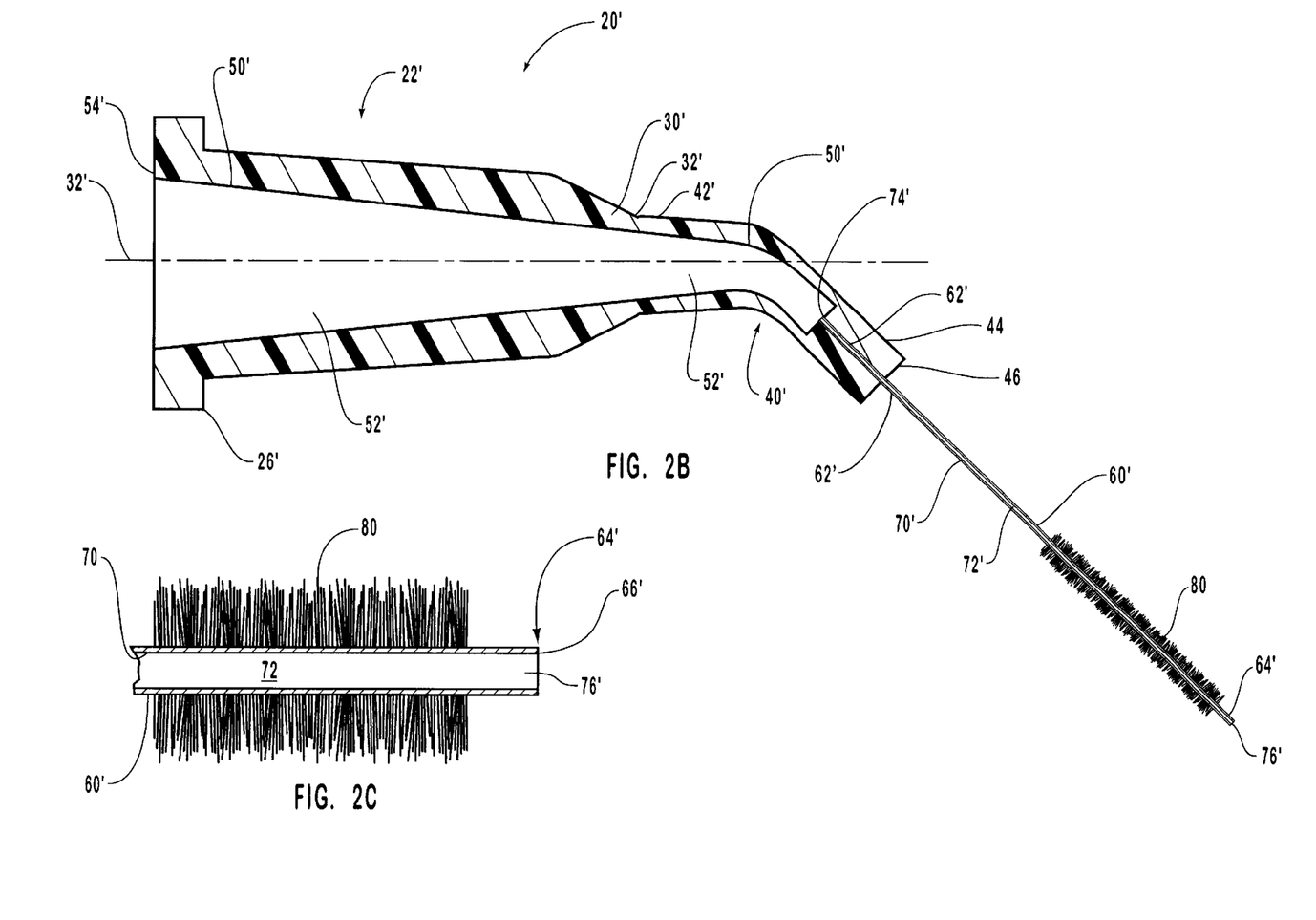
FIG. 2B is a cross sectional view of the endodontic irrigation tip shown in FIG. 2A.
FIG. 2C is an enlarged cross sectional view of the distal insertion end shown in FIG. 2A.
Figure 4:
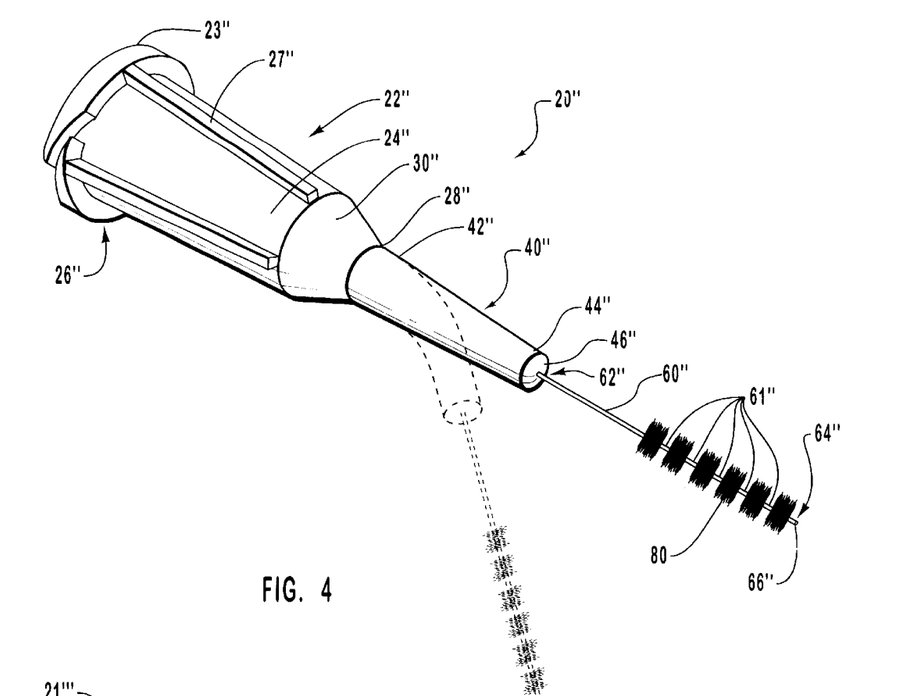
FIG. 4 is a perspective view of another embodiment of the present invention featuring a selectively bendable neck with fibers on the cannula in symmetrically spaced bands.
Figure 5:
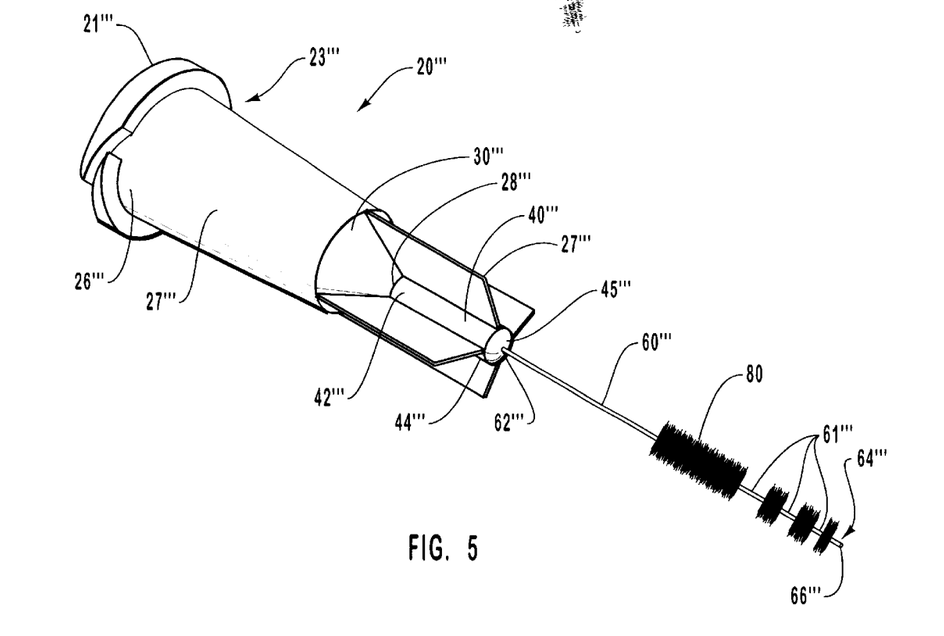
FIG. 5 is a perspective view of another embodiment of the present invention with fibers on the cannula in bands that have various widths or lengths.
Figure 6A:
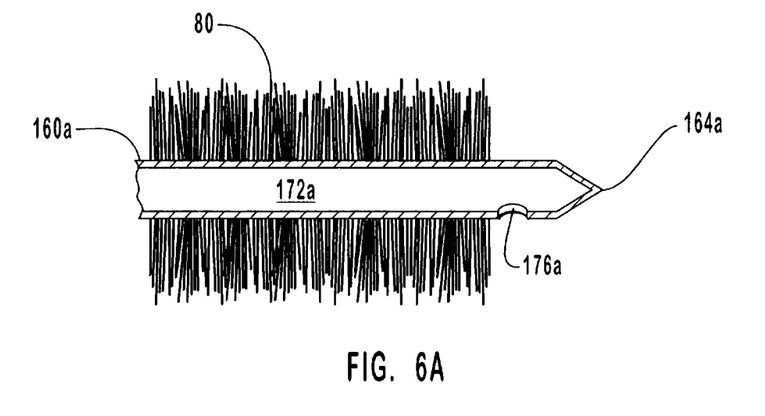
FIG. 6A provide is a cross sectional view of a distal insertion end of an irrigation tip.
Figure 6B:
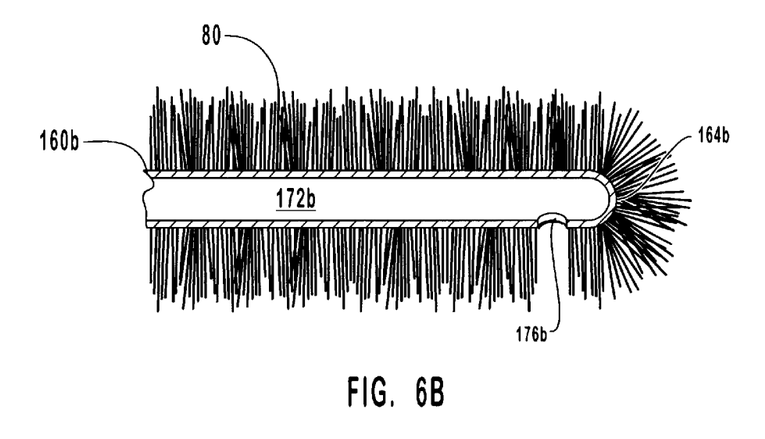
FIG. 6B is a cross sectional view of a distal insertion end of another irrigation tip.
Figure 6C:
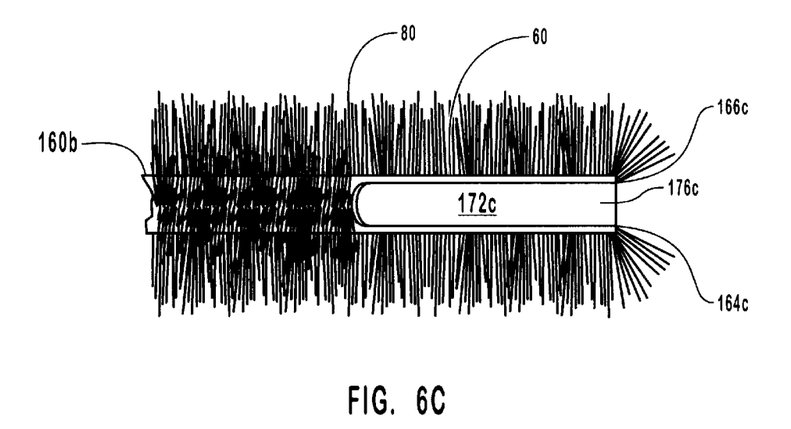
FIG. 6C is a perspective view of a distal insertion end of another irrigation tip.

Another embodiment of the inventive endodontic irrigator tip is shown in FIGS. 2A–2C at 20'. The distal insertion ends of tips 20 and 20' are contrasted respectively in FIG. 1C and FIG. 2B. FIGS. 4–5 depict additional embodiments of irrigator tips respectively at 20" and 20'" which have bands of fibers on their respective cannulas. Each embodiment is discussed below in greater detail. Various distal insertion ends 164 of cannulas and their respective outlet orifices 176 are shown in FIGS. 6A–6C. Note that the same numerals are used to identify the corresponding elements of each embodiment with prime symbols being used to indicate the element in reference to a specific embodiment.

Figure 3A:
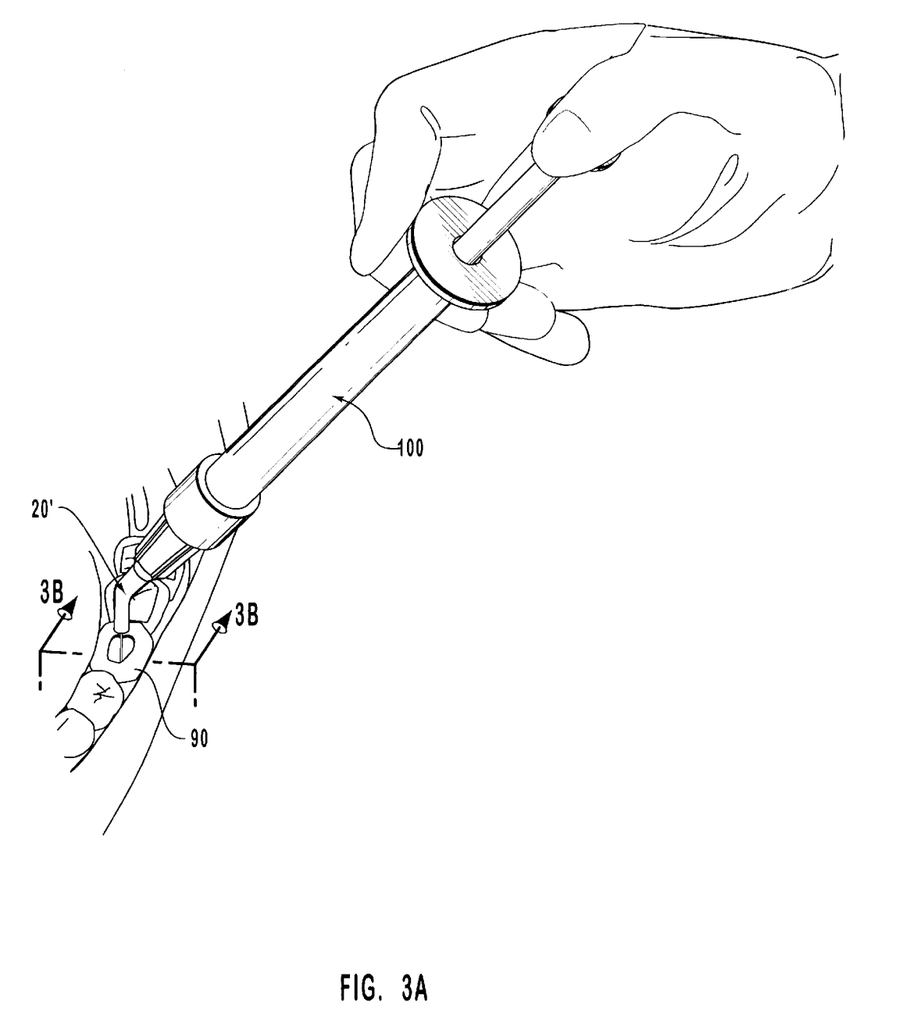
FIG. 3A depicts the endodontic irrigation tip of FIGS. 2A–2C inserted into a tooth.
Figure 3B:
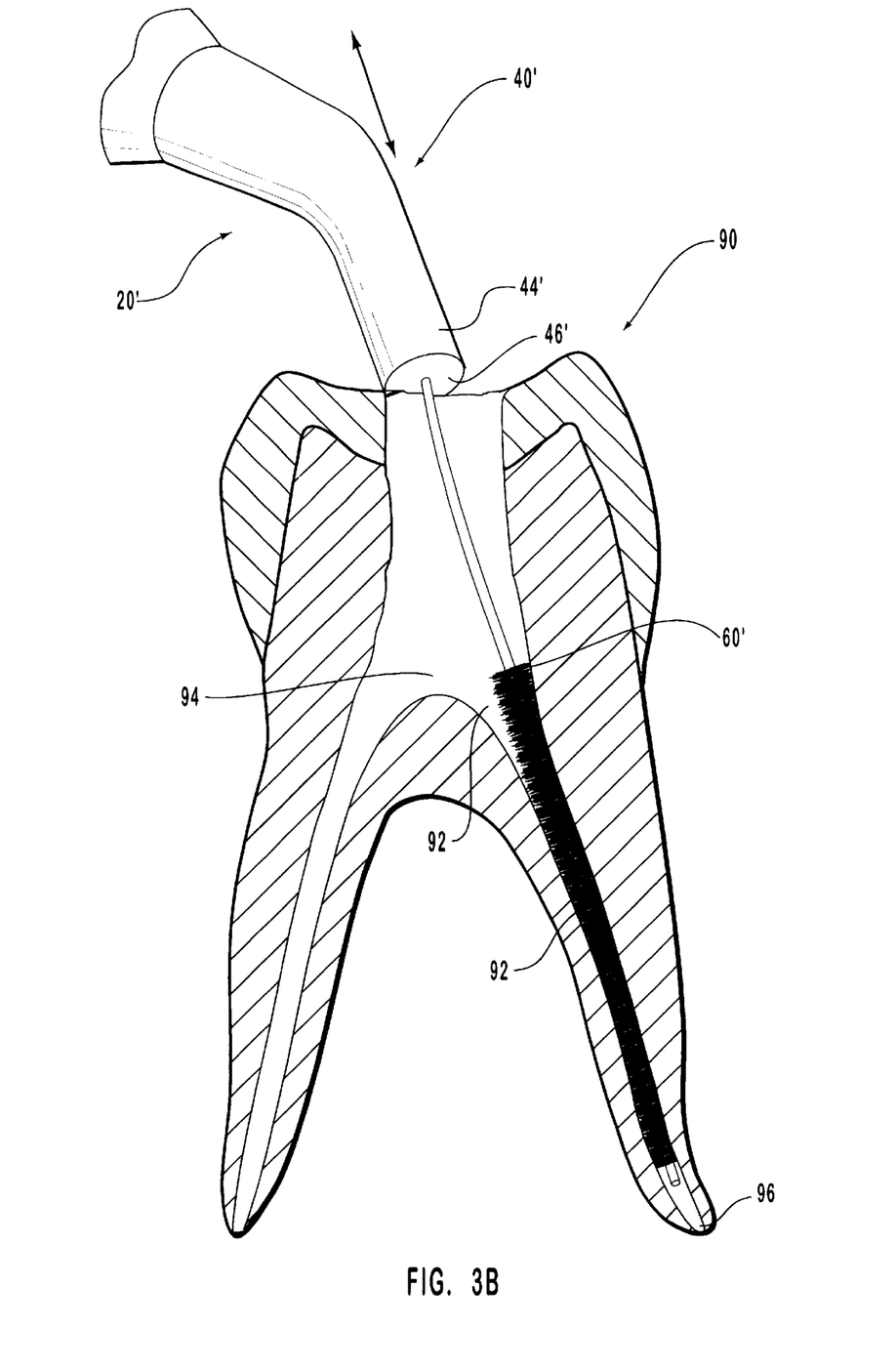
FIG. 3B is a view of a cross section of a tooth which has undergone a root canal procedure and is being irrigated by the endodontic irrigation tip of FIGS. 2A–2C.

FIGS. 3A–3B depict the advantage achieved through the use of irrigator tip 20' having a cannula 60' with fibers 80. The endodontic cannula 60' is moved up and down so that fibers 80 can brush the sides of root canal 92 of tooth 90 much like a pipe cleaner. The diameter of the endodontic cannula and the length of the fibers are selected so that when combined the fiber coated cannula can move within the root canal and effectively scrub the the sides of root canal 92. Fibers 80 are also selected to have a desired balance of rigidity and flexibility for effective scrubbing of the sides of root canal 92.

The entire cannula may be covered by fibers, however, it is generally not necessary to cover all of the cannula since the upper portion of the cannula is not in the root canal. More particularly, once the distal insertion end as shown at 64' in FIG. 3B is directed toward the apex of root canal 92, then the upper portion is adjacent the opening formed through the crown of the tooth and the pulp chamber 94. Since the opening and the pulp chamber 94 are accessible, it is not necessary to clean this portion of the tooth in the same manner as the root canal located below pulp chamber 94 and extending to apex 96. Accordingly, the portion of the cannula that is intended for insertion into root canal 92 is preferably covered with fibers while the portion thereabove does not necessarily require fibers for effective usage of the cannula.

The portion of the cannula that is covered by fibers is preferably long enough such that the cannula need only be moved slightly up and down within the cannula in order to brush the root canal. Accordingly, the length of the fiber covered portion preferably corresponds approximately to the length of the root canal, the length from the apex up to the pulp chamber of the tooth. When the fiber covered portion has such a length, any up and down movement of the cannula enables the root canal to be brushed. Of course, it is desirable to minimize the need for up and down movement within the root canal as such movement increases the risk of ledging within the root canal or crimping the cannula. Since about half of the length of the cannula is used to extend beyond the pulp chamber and into the root canal, the fiber covered portion of the cannula preferably has a length that is about one-half of the working length of the cannula. As shown in FIG. 3B, more than about half of the working length may be need to extend into the root canal as desired. Although, the fiber covered portion preferably corresponds with the root canal length, the fiber covered portion may be much shorter. For example, effective brushing may still be achieved when only about one-quarter of the cannula is covered with fibers. However, when less than about one-fifth of the cannula is covered then the cannula must be moved more than is desired within the root canal in order to brush all of the root canal. Accordingly, the fiber covered portion is preferably more than about one-fifth of the working length of the cannula, preferably at least about one-quarter of the working length of the cannula and most preferably at least about one-half of the working length.

In all of these embodiments, the fibers are positioned around the circumference of at least a portion of the cannula and extend from the cannula with a length that enables the fibers to engage surfaces of the root canal in a scrubbing action as the cannula is moved up and down within the root canal. The primary difference between the position of the fibers 80 on cannula 60 and the position of the fibers on the other embodiments is that cannula 60 is covered by fibers from its distal insertion end 64 along the portion of cannula 60 intended for insertion into the root canal while the other embodiments have no fibers in the immediate vicinity of the outlet orifices 76 of their respective cannula 60.

Cannulas 60', 60" and 60''' each have fibers that are positioned sufficiently far above the distal insertion end such that there are no fibers in the immediate vicinity of the outlet orifice 76 and such that the distal insertion end 62 can directly contact root canal surfaces. This configuration may be useful in some circumstances. FIG. 3B shows cannula 60' inserted into root canal 92 such that distal insertion end 62' is about 2 mm to about 3 mm away from apex 96. This distance corresponds with the height of most apical constriction above the apex of most root canals. A cannula having all of its lower portion covered, such as cannula 60, can also generally be inserted as far as most conventional irrigator tips are inserted. However, since it is easier to insert a cannula into the root canal toward the apex if the cannula has a relatively small diameter, in some instances it may be preferable not to place fibers on the distal insertion end as the distal insertion end may otherwise be to large to extend toward the apex.

In some instances, it may be preferable for the practitioner to optimally feel the progress of the distal insertion end of the cannula in the root canal by maintaining the distal insertion end of the cannula such that it is not covered with fibers. It may also be advantageous not to position fibers in the immediate vicinity of the outlet orifice of the cannula such as outlet orifice 76', 76''', and 176' as the flow of the fluid is less likely to become blocked due to root canal debris. More particularly, it avoids the possibility of soft material becoming clogged in fibers around the outlet orifice of the cannula.

Apical extrusion occurs when root canal material such as necrotic pulp material is pushed out of the apex and into the periapical tissue surrounding the apex of the root canal. Such an extrusion of infected material beyond the apex is very undesirable as it may cause chronic tissue inflammations. Apical extrusion can cause the root canal procedure to fail and especially, especially in an infected root canal with apical complications. This can be avoided by selecting an endodontic irrigator tip that has an appropriate length and outer diameter for the particular root canal and then appropriately using the irrigator tip. In addition to the length and the outer diameter of the cannula, the potential for causing an apical extrusion may be further minimized through arrangement of the fibers and the configuration of the outlet orifice.

Fibers 80 extend from the cannula with a distance that is sufficient to enable the fibers to engage the root canal surfaces, particularly the sidewalls in the upper portion of the canal below the pulp chamber. More particularly, the length is sufficient for a scrubbing action that enables soft material in the root canal to be removed. The fibers may extend with a length in a range about 0.3 mm to about 3 mm, preferably from about 0.5 mm to about 2 mm, more preferably from about 0.7 mm to about 1.5 mm, such as about 1 mm, for example. Fibers 80 can also have a variety of different lengths. In one embodiment, short and long fibers exist in a particular bundle of fibers such that the long fibers are supported by the short fibers. The fibers on a cannula may also have either the same diameter or a plurality of diameters. The diameter may range from about 1 Denier to about 15 Denier, and is more preferably in the range from about 1.5 Denier to about 10 Denier.

Both synthetic and natural fibers may be used. Suitable synthetic fibers include nylon and polyester fibers while suitable natural fibers include cotton fibers. The fibers may optionally be formed from polypropylene, polyethylene or another thermoplastic elastomer material having a hardness comparable to polypropylene or polyethylene.

Fibers 80 can be affixed to coating 38 in a variety of different well known methods such as through electrostatic flocking. According to one flocking method, an adhesive is applied to cannula 60 where fiber attachment is desired. The adhesive used to attach fibers 80 to cannula 60 is preferably water insoluble, for example, the adhesive may be polyurethane. A polyurethane adhesive has a desired degree of flexibility and water insolubility. An acrylic adhesive maybe used that is flexible. Such adhesives are preferably light cured. Other adhesives that may be useful include epoxies and silicones, although, these are generally less flexible. An appropriate quantity of fibers is then contacted with the adhesive material. The adhesive is allowed to harden, thereby securing the fibers to the desired portion. Further information regarding methods for adhering fibers to a cannula can be obtained from U.S. patent application Ser. No. 09/702,284 entitled Cushioned, Fiber-Covered Dental Applicators filed on Oct. 30, 2000 and U.S. patent application Ser. No. 09/496,275 entitled Electrostatically Flocked Fishing Lures and Related Systems and Methods, both of which are hereby incorporated by reference. An additional method of fiber attachment is to injection or insertion mold the fibers onto the desired cannula. Thus, in one embodiment, the fibers are in a diameter and length which allows injection or insertion molding. Cannula 80 is preferably formed from stainless steel, however, it may also be a plastic material, that is either the same or a different plastic material from that used to form the fibers.

Fibers 80 preferably extend perpendicularly with respect to cannula 60 as shown. However, the fibers may also extend with other orientations such as a slanted configuration such that the fibers extend downward toward the distal delivery end or upward toward the proximal end of cannula 60.

The fibers may have any suitable density. However, the fibers are preferably dense enough to enable soft material in the root canal to be retained by the fibers such that some of the soft material may be removed from the root canal by pulling the cannula out of the root canal.

While the endodontic irrigator tip may have many suitable configurations, irrigator tip 20 and tip 20' are described in detail in order to provide disclosure of preferred configurations. Note that irrigator tip 20' has a hub that is configured similarly to the hub of the irrigator tip discussed in U.S. Pat. No. 6,079,979 entitled Endodontic Irrigator Tips and Kits which issued to Francesco Riitano and is owned by Ultradent Products Inc. U.S. Pat. No. 6,079,979 is hereby incorporated by reference. It should be understood that reference to an element and its corresponding number as shown in the drawings is also descriptive of the same element in other embodiments unless indicated otherwise by particular reference to the element. Accordingly, reference is made primarily to the configuration of tip 20 and its elements are discussed and contrasted with the corresponding elements of the other embodiments, primarily tip 20'. The features of the elements disclosed herein may be combined in any suitable fashion so, for example, cannula 60' may have a rounded rim defog its outlet orifice like rounded rim 66 instead of squared rim 66'. Similarly, cannula 60' may have fibers on all of its lower half, along its entire length or in bands such as the configurations of cannulas 60" and 60'''.

p The hub is preferably designed to be coupled to means for dispensing fluid to the tip. Examples of the means for dispensing fluid to the tip include a syringe, a ratcheting device which increases in pressure upon ratcheting to deliver liquid, or a threaded plunger. Hub 22 further includes a male or female Luer lock component 23, or a standard thread which mates with another thread to engage the syringe or similar device. Such lock components and standard threads are examples of means for coupling the proximal end of the hub to the fluid dispensing means. The hub preferably has a feature that provides a grasping surface for positioning the tip on a syringe. Hub 22 has wings 27 extending longitudinally from body 24 while hub 22' has ridges 27' extending longitudinally from body 24" and neck 40". The hub may also be an integral extension of a device such as a syringe. Of course a hub that is integral with a syringe does not need grasping surfaces such as wings 27 or ridges 27'.

Hub 22 has two primary components including body 24 and neck 40. Body 24 and neck 40 are depicted in FIG. 1A as integral components and accordingly body 24 and neck 40 are essentially portions of hub 22. Hub 22' also has an integral body 24' and neck 40'. Neck 40 is straight while neck 40' is the portion of hub 22' that is angled. The neck is preferably at 3 narrower than body 24, as depicted, in both embodiments. Although the body and the neck are depicted as integral portions of the hub, each may also be separate components. Accordingly, the body and the neck are discussed herein with reference to their respective proximal and distal ends.

Each body 24 has a proximal end 26 opposite from a distal end 28, the proximal end being the proximal end of the hub. Body 24 may also include a shoulder 30, which is a tapered portion of body 24, as shown by the embodiment depicted in FIG. 1A at 30. Although shoulder 30 is not necessary, it is preferred as it provides a gradual transition to neck 40. Note that the longitudinal axis of body 26' is identified at 32' to provide reference to the angled orientation.

Neck 40 of hub 22 has a proximal end 42 coupled to distal end 28 of body 24. Each neck has a distal end 44 opposite proximal end 42 which is the distal end of the hub. Note that the proximal end of hub 22 is proximal end 26 of body 24 and distal end of hub 22 is distal end 44 of neck 40. In one embodiment, the length of the neck 40 or 40' is in the range of about 3 to about 20 millimeters, more preferably about 4 to about 15 millimeters, and most preferably about 5 to about 12 millimeters.

A round nib 45 extends from distal end 44 around proximal end 62 of cannula 60 which is an exposed portion of a plug used to assist in retaining cannula 60 and in providing a seal around cannula 60. The plug is an adhesive that has been cured after the cannula has been positioned within neck 40. Any suitable adhesive may be utilized such as commercially available epoxies intended for gluing stainless steel to plastics such as polypropylene. Note that in contrast to the configuration of distal end 44, the distal end of neck 40' is a distal stop end 44' with a flat distal face 46'. The advantages of flat distal face 46' are discussed below in greater detail.

A cross-sectional view of hub 22 is not provided so the interior configuration of the is described in reference to hub 22' and the cross-sectional view thereof shown in FIG. 2B, however, hub 22 has a similar configuration and similar elements. Hub 22' has an interior surface 50' within body 24' and neck 40' that defines a hollow chamber 52'. Hollow chamber 52' has an inlet 54' that is an opening into hollow chamber 52' for fluid communication with the means for dispensing fluid to the tip. Hollow chamber 52' is an example of a chamber means for containing fluid within the hub as received from the means for dispensing fluid to the endodontic irrigator tip.

Cannula 60 has a proximal end 62 opposite a distal insertion end 64. A portion of proximal end 62 is sheathed within distal end 44 of neck 40 such that a portion of cannula 60 extends from distal end 44 of neck 40 with sufficient length to extend into a root canal of a tooth. Cannula 60 has an outer diameter which permits insertion of cannula 60 into a root canal of a tooth. Of course, it is preferable for cannula 60 to be generally flexible for advancement within a root canal.

Cannula 60 has an interior surface 70 defining a conduit 72. As best view and described in relationship to FIG. 2B, fluid enters conduit 72' from hollow chamber 52' via an inlet 74' located at proximal end 62' such that conduit 72' and hollow chamber 52' are in fluid communication. Fluid exits conduit 72' via outlet orifice 76' at distal insertion end 64', as best viewed in FIG. 2C or in FIG. 1B for tip 20. All of the cannulas disclosed herein are examples of delivery means for delivering fluid from the chamber means to a root canal of a tooth while inserted within the root canal.

Cannula 60 can be coupled to neck 40 in a fluid tight manner through a variety of means. In one embodiment, cannula 60 comprises a metal material while hub 22 is comprised of polycarbonate or another rigid material. In another embodiment, cannula 60 extends integrally from hub 22. The gauge of cannula 60 may be, for example, in the range of about 33 to about 18 gauge, more preferably about 31 to about 25 gauge, and most preferably, about 31 to about 27 gauge.

Cannula 60 is substantially straight and has a portion sheathed within distal end 44. An advantage of the configuration of tip 20' as shown best in FIG. 2B, is that cannula 60' is angled with respect to the longitudinal axis 32' of body 24' while distal stop end 44' is perpendicular with respect to cannula 60'. Due to the angled configuration, as shown in FIGS. 3A–3B, a practitioner is readily able to place the angled tip 20' into a root canal of a patient's tooth 90 while holding a syringe 100 coupled to tip 20' at an angle with respect to the patient's mouth. This angled configuration enables the practitioner to more easily insert the tip into a root canal and to move the tip within the root canal. Further, this angled configuration is particularly useful when moving the fiber coated cannula 60' in an up and down movement within the root canal 92 to enable fibers 80 to brush against the root canal surfaces.

Distal stop end 44' is angled with respect to longitudinal axis 32' at any suitable angle. By way of example, in one embodiment the angle α is in the range of about 45° to about 180°, more preferably, about 60° to about 160°, most preferably, about 90° to about 140°. In the embodiment shown in FIGS. 2A–2B, the angle α is about 120°. The angle preferably enables a practitioner to maneuver the tip without concern for the position of structures other than the tooth being treated. For example, as shown in FIG. 3A, tip 20' can be moved while treating tooth 90 without any contact with the teeth on the opposite jaw by the practitioner's hand, syringe 100 or tip 20'.

Distal stop end 44' of neck 40' has a diameter that is substantially greater than the outer diameter of cannula 60'. Thus, as shown in FIGS. 3A–3B, distal stop end 44' acts as an integral stop to prevent penetration into the root canal 92 of endodontic irrigator tip 20' beyond the length of the portion of cannula 60' extending from distal stop end 44' of neck 40'. As shown, the practitioner is able to strategically, conveniently position distal stop end 44' on the rim of the occlusal surface of a crown and orient cannula 60' in a controlled manner within root canal 82'.

As shown, flat distal face 46' of distal stop end 44' is substantially perpendicular to cannula 60'. Since face 46' is oriented substantially perpendicular to cannula 60', face 46' can be reliably positioned in a secure manner on the crown of a tooth. The stop prevents apical perforation since only the portion of cannula 60 extending from the stop can be inserted into the root canal. This is particularly advantageous when moving the cannula in an up and down motion within root canal 92 in order to enable fibers 80 to brush the root canal surfaces.

The working length of cannula 60 is the portion of cannula 60 extending past distal end 44 of neck 40. As discussed above, the practitioner is able to avoid apical perforations by using an irrigator tip having a cannula with the appropriate working length. Of course, this is enhanced by using a tip having an integral stop such as distal stop end 44'.

The appropriate working length of the cannula is determined by viewing radiographic images of the tooth. As shown by the lengths listed below in Table 1 for average root canal lengths encountered for a particular type of tooth, root canal lengths vary significantly based on the type of tooth.

TABLE 1

Average Root Canal Lengths

| Tooth | Upper | Lower |
| --- | --- | --- |
| Central | 23 mm | 20.5 mm |
| Lateral | 22 mm | 21 mm |
| Canine | 26.5 mm | 25.5 mm |
| First Premolar | 20.5 mm | 20.5 mm |
| Second Premolar | 21.5 mm | 22 mm |
| First Molar | 20.5 mm | 21 mm |
| Second Molar | 20 mm | 20 mm |

Since various lengths are encountered, endodontic irrigator tips are preferably supplied in a kit with tips that have various cannula lengths. Such a kit can be used for root canals of all different lengths. Thus, in one kit for example, tips 20 are featured having working cannula lengths (i.e., the portion of cannula 60 extending past distal end 44 of neck 40) of about 17 mm, about 21 mm and about 25 mm.

Of course, the cannulas may have a broader range of working lengths depending on the manner in which the cannula is inserted into the root canal. For example, cannula 60 may have a working length ranging from about 10 to about 35 millimeters, from about 12 to about 30 millimeters, or from about 14 to about 28 millimeters. Additionally, the kit may include a large number of tips wherein the length of each cannula increases incrementally, for example, about 0.5 mm to about 1 mm, between each subsequent tip in the kit, such that the kit includes working cannula lengths about 17, about 17.5 mm, about 18 mm, and so on up to about 25 mm in increments of one-half a millimeter.

Because the kit features different cannula working lengths, the practitioner can choose the working length of a cannula needed for any root canal procedure, fine tuning the working length of each tip, such that the cannula selected delivers fluid to the precisely desired location. The kit can thus be used in root canals having a variety of different lengths.

FIG. 1B is an enlarged, cross-sectional view of the distal insertion end 64 of cannula 60 shown in FIG. 1A. Note that FIG. 2C depicts an enlarged, cross-sectional view of the distal insertion end 64' of cannula 60' shown in FIGS. 2A–2B. In the embodiment depicted in FIG. 1B, distal insertion end 64 has a rounded rim 66 which defines outlet orifice 76 in contrast to the conventional squared rim 66' of distal insertion end 64' shown in FIG. 2C. While a squared rim may be utilized, the rim is preferably round. The curved or bull nose configuration of rounded rim 66 is highly advantageous when moving cannula 60 in an up and down fashion. More particularly, the more frequently that fiber covered cannula 60 is moved up and down within root canal 92, the greater the likelihood of causing ledging. As discussed above, ledges can occur when a practitioner attempts to insert the distal insertion end of an irrigator tip as far as the apex of the root canal and the distal insertion end is halted prematurely against the sidewall of the root canal. The downward pressure exerted on the distal insertion end can cause the distal insertion end to dig into the side of the root canal and form a ledge. Such ledges are difficult to bypass; and if the ledge occurs very close to the apex, the ledge may give the practitioner the mistaken impression that the apex has been reached. The curved configuration of rounded rim 66 provides less frictional contact than does squared rim 66' and therefore minimizes the potential for causing ledging. So when resistance is encountered, it is easier for the distal insertion end 64 with rounded rim 66 to slide off or around the structure in the root canal that has blocked its path and to then progress further down into the root canal.

Rounded rim 66 may be formed by any suitable methodology. One method involves mounting hub 22 on a rotating spindle and then spinning the rim against a curved abrasive structure configured to round off the squared edge.

Like endodontic irrigator tip 20', the endodontic irrigator tip shown in FIG. 4 at 20" also has a cannula with no fibers at the distal insertion end. The fibers may be positioned on the cannula such that there are no fibers within about 1 mm of the distal insertion end, not within about 1.5 mm of the distal insertion end, not within about 2 mm of the distal insertion end or not within about 3 mm of the distal insertion end. The fiberless configuration of the distal insertion end may also be described by understanding that the fibers have an attachment end and a brush end and that the fibers are positioned on the cannula such that no brush ends of the fibers reach within about 1 mm of the distal insertion end, not within about 1.5 mm of the distal insertion end, not within about 2 mm of the distal insertion end or not within about 3 mm of the distal insertion end. The fiberless configuration of the distal insertion end may also be described as having no fibers above the outlet orifice for a length that is at least about twice or at least about three times that of the outer diameter of the rim that defines the outlet orifice.

As shown in FIG. 4, hub 22" is constructed similarly to hub 22' except that neck 40' is disclosed as being rigid and angled while neck 40" may be either rigid and straight or flexible. It may be flexible so that it can be selectively bent to a desired location by the practitioner, yet be sufficiently rigid to remain in the desired location until bent again by the practitioner. Accordingly, neck 40" may be formed from a rigid plastic which can become bendable upon heating and then rigid again after subsequent cooling.

Endodontic irrigator tip 20''' has a hub 22''' that is constructed similarly to hub 22. Note however that hub 22''' has four wings 27''' that extend longitudinally only from neck 40'''.

The endodontic irrigator tips 20" and 20''', respectively shown in FIG. 4 and FIG. 5, each have a cannula with bands of fibers 80 separated by portions of the cannula that are not covered by fibers as identified at 61' and 61'''. The bands of fibers 80 on cannula 60' have equal lengths or widths and are also equally spaced apart from each other. In contrast, the bands of fibers 80 on cannula 60''' have different widths and are not equally spaced apart. The spacing may be usefuil for holding soft material and removing the soft material from the root canal.

Since the majority of the soft material in the root canal is in the portion of the root canal above the apical portion, it is preferable to have fibers on the cannula positioned to engage this portion of the root canal. Accordingly, fibers may be positioned as shown on cannula 60 so that all of the surfaces of the root canal above the apex are continuously brushed or the user may rely on the up and down movement of alternating fiber coated surfaces of cannulas such as cannula 60' and 60" to engage all of the surfaces of the root canal above the apex.

FIGS. 6A–6C depict a plurality of cannulas 160*a*–*c* having various distal insertion ends 164*a*–*c* and various outlet orifices 176*a*–*c*. Cannula 160*a* has a pointed distal insertion end 164*a* adapted for aggressive movement within the root canal while cannula 160*b* has a rounded distal insertion end. Note that both distal insertion end 164*a* and 164*b* are closed so that the outlet orifices 176*a* and 176*b* are in the sidewalls of their respective cannulas. This sideported configuration is useful in some circumstances, particularly when working very close to the apex as it buffers the impact of the flow of the liquid, thereby minimizing the likelihood of apical perforation. The fibers may covered the cannula in the vicinity of the outlet orifice and the distal insertion end as shown in FIG. 6B or the fibers may only be positioned above the outlet orifice as shown in FIG. 6A. FIG. 6C depicts another embodiment wherein the outlet orifice is a slot 176*c* extending from the distal insertion end upward and tapering into the sidewall of cannula 160*c* such that a portion of conduit 172*c* is exposed. Fibers extend perpendicularly in a circumferential configuration from cannula 160*c* such that slot 176*c* is surrounded by fibers and such that the portion above the distal insertion end 164*c* is covered by fibers.

The last several millimeters of the cannula may also be annealed to provide for greater flexibility at the distal portion of the cannula. Additional details regarding annealed cannulas are provided in U.S. patent application Ser. No. 09/entitled Endodontic Irrigator Tips Having Cannulas With Annealed Distal Portions and Related Methods which was filed on January___, 2001. Serial No. 09/is hereby incorporated by reference The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for irrigating a root canal, comprising:
   obtaining an endodontic irrigator tip having a cannula extending from a hub, the cannula having fibers positioned around the circumference of at least a portion of the cannula;
   inserting the cannula of the endodontic irrigator tip into a root canal after the root canal has been abrasively cleaned with an appropriate instrument;
   delivering an irrigant through a conduit in the cannula and out of an outlet orifice at a distal insertion end of the cannula such that the irrigant is delivered into the root canal; and
   brushing root canal surfaces with the fibers as the cannula is moved up and down within the root canal to further clean the root canal.

2. A method as recited in claim 1, further comprising the step of removing the cannula from the root canal in order to remove soft material from the root canal that is retained by the fibers.

3. A method as recited in claim 1, wherein the fibers are dense enough to enable soft material in the root canal to be retained by the fibers such that some of the soft material may be removed from the root canal by pulling the cannula out of the root canal.

4. A method as recited in claim 1, wherein the fibers extend circumferentially from the cannula along at least one-fifth of the cannula.

5. A method as recited in claim 1, wherein the fibers extend circumferentially from the cannula along at least one-quarter of the cannula.

6. A method as recited in claim 1, wherein the fibers extend circumferentially from the cannula along the lower half of the cannula.

7. A method as recited in claim 1, wherein the fibers are positioned sufficiently far above the distal insertion end of the cannula such that there are no fibers in the immediate vicinity of the outlet orifice of the cannula and such that the distal insertion end of the cannula directly contacts root canal surfaces.

8. A method as recited in claim 1, wherein the outlet orifice is defined by a rim and wherein the fibers are sufficiently far above the distal insertion end that there are no fibers for a length that is at least about twice that of the outer diameter of the rim.

9. A method as recited in claim 1, wherein the fibers are positioned on the cannula through a flocking process.

10. A method as recited in claim 1, wherein the cannula has a length in a range from about 10 millimeters to about 35 millimeters.

11. A method as recited in claim 1, wherein the conduit in the cannula has a gauge in a range from about 33 gauge to about 18 gauge.

12. A method as recited in claim 1, wherein the outlet orifice is defined by a rounded rim.

13. A method as recited in claim 1, wherein the outlet orifice is defined by a squared rim.

14. A method as recited in claim 13, wherein the fibers are positioned on the cannula such that there are no fibers within 2 mm of the distal insertion end.

15. An endodontic irrigator tip for use in conjunction with means for dispensing fluid to the endodontic irrigator tip, the tip comprising:
   a hub having a proximal end opposite from a distal end;
   means for coupling the proximal end of the hub to means for dispensing fluid to the irrigator tip;
   chamber means for containing fluid within the hub as received from the means for dispensing fluid to the endodontic irrigator tip;
   delivery means for delivering fluid from the chamber means to a root canal of a tooth while inserted within the root canal, the delivery means extending from the distal end of the hub with a length and outer diameter that permits insertion of the delivery means into a root canal of a tooth, wherein the delivery means terminates at a distal insertion end, wherein the delivery means has a conduit defined by an interior surface of the delivery means, wherein the conduit has an inlet that is in fluid communication with the chamber means of the hub, wherein the conduit terminates at an outlet orifice such that fluids can be delivered from the hollow chamber, through the conduit and then out of the outlet orifice; and fibers positioned around the circumference of the delivery means such that no less than about one-fifth of the length of the delivery means is covered by the fibers, wherein the fibers extend from the delivery means with a length that enables the fibers to engage surfaces of the root canal in a scrubbing action as the delivery means is moved up and down within the root canal.

16. An endodontic irrigator tip as recited in claim 15, wherein the fibers are configured to enable soft material in the root canal to be retained by the fibers such that some of the soft material may be removed from the root canal by pulling the delivery means out of the root canal.

17. An endodontic irrigator tip as recited in claim 15, wherein the fibers extend circumferentially from the delivery means along at least one-quarter of the delivery means.

18. An endodontic irrigator tip as recited in claim 15, wherein the fibers extend circumferentially from the delivery means along at least one-half of the delivery means.

19. An endodontic irrigator tip as recited in claim 15, wherein the fibers are positioned on the lower half of the delivery means.

20. An endodontic irrigator tip as recited in claim 15, wherein the fibers are positioned sufficiently far above the distal insertion end of the delivery means such that there are no fibers in the immediate vicinity of the outlet orifice of the delivery means and such that the distal insertion end of the delivery means can directly contact root canal surfaces.

21. An endodontic irrigator tip as recited in claim 15, wherein the fibers have an attachment end and a brush end, wherein the fibers are positioned on the delivery means such that no brush ends of the fibers reach within 1 mm of the distal insertion end.

22. An endodontic irrigator tip as recited in claim 15, wherein the outlet orifice is defined by a rim and wherein the fibers are sufficiently far above the distal insertion end that there are no fibers for a length that is at least about twice that of the outer diameter of the rim.

23. An endodontic irrigator tip as recited in claim 15, wherein the fibers are positioned on the delivery means through a flocking process.

24. An endodontic irrigator tip as recited in claim 15, wherein the delivery means has a length in a range from about 10 millimeters to about 35 millimeters.

25. An endodontic irrigator tip as recited in claim 15, wherein the conduit in the delivery means has a gauge in a range from about 33 gauge to about 18 gauge.

26. An endodontic irrigator tip as recited in claim 15, wherein the outlet orifice is defined by a rounded rim.

27. An endodontic irrigator tip for use in conjunction with means for dispensing fluid to the endodontic irrigator tip, the tip comprising:
   a hub having a proximal end opposite from a distal end, wherein the hub has a hollow chamber defined by an interior surface of the hub, wherein the hollow chamber has an inlet that is an opening into the hollow chamber for fluid communication with a means for dispensing fluid to the endodontic irrigator tip;
   means for coupling the proximal end of the hub to the means for dispensing fluid to the irrigator tip;
   a cannula extending from the distal end of the hub with a length and outer diameter that permits insertion of the cannula into a root canal of a tooth, wherein the cannula terminates at a distal insertion end, wherein the cannula has a conduit defined by an interior surface of the cannula, wherein the conduit has an inlet that is in fluid communication with the hollow chamber of the hub, wherein the conduit terminates at an outlet orifice such that fluids can be delivered from the hollow chamber, through the conduit and then out of the outlet orifice; and
   fibers positioned around the circumference of the cannula such that no less than about one-fifth of the length of the cannula is covered by the fibers, wherein the fibers extend from the cannula with a length that enables the fibers to engage surfaces of the root canal in a scrubbing action as the cannula is moved up and down within the root canal.

28. An endodontic irrigator tip as recited in claim 27, wherein the fibers are configured to enable soft material in the root canal to be retained by the fibers such that some of the soft material may be removed from the root canal by pulling the cannula out of the root canal.

29. An endodontic irrigator tip as recited in claim 27, wherein the fibers extend circumferentially from the cannula along at least one-quarter of the cannula.

30. An endodontic irrigator tip as recited in claim 27, wherein the fibers extend circumferentially from the cannula along at least one-half of the cannula.

31. An endodontic irrigator tip as recited in claim 27, wherein the fibers are positioned circumferentially along the lower half of the cannula.

32. An endodontic irrigator tip as recited in claim 27, wherein the fibers are positioned sufficiently far above the distal insertion end of the cannula such that there are no fibers in the immediate vicinity of the outlet orifice of the cannula and such that the distal insertion end of the cannula can directly contact root canal surfaces.

33. An endodontic irrigator tip as recited in claim 27, wherein the fibers are positioned on the cannula such that there are no fibers within 2 mm of the distal insertion end.

34. An endodontic irrigator tip as recited in claim 27, wherein the outlet orifice is defined by a rim and wherein the fibers are sufficiently far above the distal insertion end that there are no fibers for a length that is at least about twice that of the outer diameter of the rim.

35. An endodontic irrigator tip as recited in claim 27, wherein the fibers are positioned on the cannula through a flocking process.

36. An endodontic irrigator tip as recited in claim 27, wherein the cannula has a length in a range from about 10 millimeters to about 35 millimeters.

37. An endodontic irrigator tip as recited in claim 27, wherein the conduit in the cannula has a gauge in a range from about 33 gauge to about 18 gauge.

38. An endodontic irrigator tip as recited in claim 27, wherein the outlet orifice is defined by a rounded rim.

39. An endodontic irrigator tip for use in conjunction with means for dispensing fluid to the endodontic irrigator tip, the tip comprising:
   a hub having a proximal end opposite from a distal end, wherein the hub has a hollow chamber defined by an interior surface of the hub, wherein the hollow chamber has an inlet that is an opening into the hollow chamber for fluid communication with a means for dispensing fluid to the endodontic irrigator tip;
   means for coupling the proximal end of the hub to the means for dispensing fluid to the irrigator tip;
   a cannula extending from the distal end of the hub with a length and outer diameter that permits insertion of the cannula into a root canal of a tooth, wherein the cannula terminates at a distal insertion end, wherein the cannula has a conduit defined by an interior surface of the conduit, wherein the conduit has an inlet that is in fluid communication with the hollow chamber of the hub, wherein the conduit terminates at an outlet orifice such that fluids can be delivered from the hollow chamber, through the conduit and then out of the outlet orifice, wherein the outlet orifice is defined by a rounded rim; and fibers positioned around the circumference of at least a portion of the cannula, wherein the fibers extend from the cannula with a length that enables the fibers to engage surfaces of the root canal in a scrubbing action as the cannula is moved up and down within the root canal.

* * * * *

UNITED STATES PATENT AND TRADEMARK OFFICE
CERTIFICATE OF CORRECTION

PATENT NO. : 6,343,929 B1
DATED : February 5, 2002
INVENTOR(S) : Dan E. Fischer

It is certified that error appears in the above-identified patent and that said Letters Patent is hereby corrected as shown below:

Column 4,
Line 46, change "need" to -- needed --

Column 11,
Line 2, change "usefuil" to -- useful --

Signed and Sealed this

Fourth Day of June, 2002

*Attest:*

*Attesting Officer*

JAMES E. ROGAN
*Director of the United States Patent and Trademark Office*